(12) United States Patent
Chen et al.

(10) Patent No.: US 8,559,597 B2
(45) Date of Patent: Oct. 15, 2013

(54) XRF SYSTEM HAVING MULTIPLE EXCITATION ENERGY BANDS IN HIGHLY ALIGNED PACKAGE

(75) Inventors: Zewu Chen, Schenectady, NY (US);
David M. Gibson, Voorheesville, NY (US); Walter M. Gibson, Voorheesville, NY (US); Adam Bailey, Albany, NY (US); R. Scott Semken, Lappeenranta (FI); Kai Xin, Wynantskill, NY (US); John H. Burdett, Scotia, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 260 days.

(21) Appl. No.: 12/920,641

(22) PCT Filed: Mar. 3, 2009

(86) PCT No.: PCT/US2009/035847
§ 371 (c)(1),
(2), (4) Date: Feb. 4, 2011

(87) PCT Pub. No.: WO2009/111454
PCT Pub. Date: Sep. 11, 2009

(65) Prior Publication Data
US 2011/0170666 A1    Jul. 14, 2011

Related U.S. Application Data

(60) Provisional application No. 61/033,899, filed on Mar. 5, 2008, provisional application No. 61/039,220, filed on Mar. 25, 2008, provisional application No. 61/042,974, filed on Apr. 7, 2008.

(51) Int. Cl.
*G21K 1/06*    (2006.01)

(52) U.S. Cl.
USPC .............................. 378/85; 378/121

(58) Field of Classification Search
USPC ....................... 378/84, 85, 119, 121
See application file for complete search history.

(56) References Cited

U.S. PATENT DOCUMENTS

| 6,014,423 A | 1/2000 | Gutman et al. ................. 378/85 |
| 6,023,496 A * | 2/2000 | Kuwabara ....................... 378/45 |

(Continued)

OTHER PUBLICATIONS

Written Opinion of the International Searching Authority and International Search Report for PCT/US2009/035847 dated Aug. 10, 2009.

*Primary Examiner* — Courtney Thomas
(74) *Attorney, Agent, or Firm* — Jeff Klembczyk; Kevin P. Radigan, Esq.; Heslin Rothenberg Farley & Mesiti P.C.

(57) ABSTRACT

An x-ray analysis apparatus for illuminating a sample spot with an x-ray beam. An x-ray tube is provided having a source spot from which a diverging x-ray beam is produced having a characteristic first energy, and bremsstrahlung energy; a first x-ray optic receives the diverging x-ray beam and directs the beam toward the sample spot, while monochromating the beam; and a second x-ray optic receives the diverging x-ray beam and directs the beam toward the sample spot, while monochromating the beam to a second energy. The first x-ray optic may monochromate characteristic energy from the source spot, and the second x-ray optic may monochromate bremsstrahlung energy from the source spot. The x-ray optics may be curved diffracting optics, for receiving the diverging x-ray beam from the x-ray tube and focusing the beam at the sample spot. Detection is also provided to detect and measure various toxins in, e.g., manufactured products including toys and electronics.

22 Claims, 11 Drawing Sheets

(56) References Cited

U.S. PATENT DOCUMENTS 7,738,630 B2 * 6/2010 Burdett et al. .................. 378/85
2002/0064253 A1 5/2002 Gutman .......................... 378/84
2007/0165780 A1 7/2007 Durst et al. ..................... 378/84

* cited by examiner

XRF SYSTEM HAVING MULTIPLE EXCITATION ENERGY BANDS IN HIGHLY ALIGNED PACKAGE

CROSS-REFERENCE TO RELATED PATENT APPLICATIONS

This application is a continuation of PCT Application PCT/US2009/035847, filed Mar. 3, 2009, and published under the PCT Articles in English as WO 2009/111454 A1 on Sept. 11, 2009. This application claims the benefit of U.S. Provisional Patent Application Ser. No. 61/033,899, filed Mar. 5, 2008, and of U.S. Provisional Patent Application Ser. No. 61/039,220, filed Mar. 25, 2008, and of U.S. Provisional Patent Application Ser. No. 61/042,974, filed Apr. 7, 2008, each of which is hereby incorporated herein by reference in its entirety.

TECHNICAL FIELD

The present invention relates generally to x-ray analysis systems, and more particularly, to x-ray source assemblies providing multiple excitation energies to improve detection and analysis of multiple elements in homogeneous and heterogeneous sample structures.

BACKGROUND OF THE INVENTION

There is an emerging need to provide manufactured products of all types in which the levels of toxins is minimized or completely eliminated. This need has a clear underlying medical basis and is accelerated by fear and pending legislation—the results of many recent well-publicized cases of toxins in manufactured products (e.g., lead in toys). The costs of unsafe products go well beyond the health impact to include significant loss of business, permanent damage to brands and corporate image, and increased levels of corporate and personal liability.

In response to these problems, there is a growing trend of increasingly strict environmental and health regulations of consumer products around the world. The list of products regulated is rapidly increasing and the types and permitted levels of toxins are becoming more restrictive. Some industry players are going beyond the regulations for the products they distribute, by mandating even cleaner products in their supply chain. Regulations are effectively aimed at decreasing direct human exposure to toxins by reducing toxins in our environment. Several stricter standards can be traced to European environmental directives that began in the early 1990s, starting with regulations in packaging materials and batteries. In subsequent years, reductions on hazardous substances were introduced by the EU for automobiles (ELV) and two directives related to electronics (Restriction of Hazardous Substances or RoHS and Waste Electrical and Electronic Equipment or WEEE). Pending U.S. Federal legislation lowers allowable lead levels in paint on toys by a factor of six and threatens criminal prosecution for companies that violate with penalties ranging from $10 million to $100 million for a single violation. In addition, nine other known toxins are targeted for restriction, including: mercury, arsenic, cadmium, barium, and chromium.

The spread of such human health and environmental initiatives are having profound global implications on the way products are designed, manufactured, and ultimately discarded or recycled.

Current measurement methods for toxins in manufactured products do not meet the needs of the supply chain, from the factories to the ultimate consumers. Identification and measurement of toxins are needed at each step of the chain, from raw materials, to components, to finished goods. While raw-material measurements are most efficient for factories, distribution channels typically require measurements on the final product. New techniques are urgently needed to accurately, quickly, consistently, and cost-effectively measure toxins at each stage, with minimal interruptions in the flow of manufacturing and distribution of the goods. Because toys and other manufactured products often have small painted features (pigments are often the source of the toxins), it is necessary to measure small areas while differentiating the paint from the base material.

Existing low-cost methods of toxin detection are generally ineffective, e.g., swab tests. Higher-cost methods that provide the requisite accuracy are expensive and time consuming. These sometimes involve: manually scraping samples, digesting them in acids at elevated temperature and pressure, introducing them into a combustion chamber, and analyzing the combustion product. One widely used method today is inductively coupled plasma optical emission spectroscopy (ICP-OES)—a method which is expensive, destructive, and slow. Alternatively, handheld x-ray fluorescence (XRF) guns are rapid and nondestructive, but are only reliable for higher than regulated concentrations, and are averaged across large sample areas, and cannot separately evaluate paint layers.

As discussed further below, the present invention provides a measurement solution having fast, accurate results for toxins in manufactured products, enabled by sophisticated proprietary x-ray optics. Such proprietary optics typically provide 10-1,000× improvements in the ability to focus x-rays; and optic-enabled analyzers are especially suited for these targeted markets—moving measurements from the lab into the factory, field, and clinic.

In x-ray analysis systems, high x-ray beam intensity and small beam spot sizes are important to reduce sample exposure times, increase spatial resolution, and consequently, improve the signal-to-background ratio and overall quality of x-ray analysis measurements. In the past, expensive and powerful x-ray sources, such as rotating anode x-ray tubes or synchrotrons, were the only options available to produce high-intensity x-ray beams, in the laboratory. Recently, the development of x-ray optic devices has made it possible to collect the diverging radiation from an x-ray source by focusing the x-rays. A combination of x-ray focusing optics and small, low-power x-ray sources can produce x-ray beams with intensities comparable to those achieved with more expensive devices. As a result, systems based on a combination of small, inexpensive x-ray sources, excitation optics, and collection optics have greatly expanded the availability and capabilities of x-ray analysis equipment in, for example, small laboratories and in the field, factory, or clinic, etc.

Monochromatization of x-ray beams in the excitation and/or detection paths is also useful to excite and/or detect very precise portions of the x-ray energy spectrum corresponding to various elements of interest (lead, etc.). X-ray monochromatization technology is based on diffraction of x-rays on optical crystals, for example, germanium (Ge) or silicon (Si) crystals. Curved crystals can provide deflection of diverging radiation from an x-ray source onto a target, as well as providing monochromatization of photons reaching the target. Two common types of curved crystals are known as singly-curved crystals and doubly-curved crystals (DCCs). Using what is known in the art as Rowland circle geometry, singly-curved crystals provide focusing in two dimensions, leaving x-ray radiation unfocused in the third or orthogonal plane. Doubly-curved crystals provide focusing of x-rays from the source to a point target in all three dimensions. This three-dimensional focusing is referred to in the art as "point-to-point" focusing.

Commonly-assigned U.S. Pat. Nos. 6,285,506 and 7,035,374 disclose various configurations of curved x-ray optics for x-ray focusing and monochromatization. In general, these patents disclose a flexible layer of crystalline material (e.g., Si) formed into curved optic elements. The monochromating function, and the transmission efficiency of the optic are determined by the crystal structure of the optic.

The ability to focus x-ray radiation to smaller spots with higher intensities, using focusing and monochromating x-ray optics, has enabled reductions in the size and cost of x-ray tubes, and x-ray systems have therefore been proliferating beyond the laboratory to in-situ, field uses. Commonly-assigned U.S. Pat. Nos. 6,934,359 and 7,072,439, incorporated by reference herein in their entirety, disclose monochromatic wavelength dispersive x-ray fluorescence (MWD XRF) techniques and systems, using doubly curved crystal optics in the excitation and/or detection paths. The x-ray optic-enabled systems described in these patents have enjoyed widespread success beyond the laboratory, for measuring sulfur in petroleum fuels in a variety of refinery, terminal, and pipeline environments.

In such systems, precise optic alignment along an axis defined by a source and sample spot may be required, as illustrated in above-incorporated U.S. Pat. No. 7,035,374, which proposes an arrangement of curved, monochromating optics around a central axis operating according to Bragg diffraction conditions. FIG. 1a is a representative isometric view of this x-ray optic arrangement 150 having a curved optic 152, an x-ray source location 154, and an x-ray target location 156. X-ray source location 154 and x-ray target location 156 define a source-to-target transmission axis 162. Optic 152 may include a plurality of individual optic crystals 164, all of which may be arranged symmetrically about axis 162.

FIG. 1b is a cross-sectional view taken along section lines 1b-1b of FIG. 1a, wherein the surface of optic 152, x-ray source location 154, and x-ray target location 156 define one or more Rowland (or focal) circles 160 and 161 of radius R for optic 152. Those skilled in the art will recognize that the number and orientation of the Rowland circles associated with crystal optic 152, or individual crystals 164, will vary with the position of the surface of optic crystal 152, for example, the variation of the toroidal position on optic crystal 152.

The internal atomic diffraction planes of optic crystal 152 also may not be parallel to its surface. For example, as shown in FIG. 1b, the atomic diffraction planes of crystal 152 make an angle $\gamma_1$ with the surface upon which x-rays are directed, at the point of tangency 158 of the surface and its corresponding optic circle 160 or 161. $\theta_B$ is the Bragg angle for crystal optic 152 which determines its diffractive effect. Each individual optic crystal can in one example be fabricated according to the method disclosed in above-incorporated U.S. Pat. No. 6,285,506, entitled "Curved Optical Device and Method of Fabrication."

All individual crystals 164 should be aligned to the source-to-target axis 162, for proper Bragg conditions. Improvement in optic alignment, especially for such multiple-crystal optics, therefore remains an important area of interest. Another issue, which particularly affects volume manufacturing, is the need to align disparate components which may be purchased from different vendors. For example, the x-ray tubes, when purchased in quantities from a vendor, may have source x-ray spots which are not consistently centered relative to their own housings. Re-centering these x-ray tube spots is necessary, as an initial step in the alignment process for an entire x-ray source assembly.

Various optic/source combinations have already been proposed to handle thermal stability, beam stability, and alignment issues, such as those disclosed in commonly assigned U.S. Pat. Nos. 7,110,506; 7,209,545; and 7,257,193. Each of these patents is also incorporated herein by reference in its entirety. In particular, U.S. Pat. Nos. 7,209,545 (entitled "X-Ray Source Assembly Having Enhanced Output Stability, and Fluid Stream Analysis Applications Thereof") and 7,257,193 (entitled "X-Ray Source Assembly Having Enhanced Output Stability Using Tube Power Adjustments and Remote Calibration") address certain tube/optic alignment problems during source operation with real-time, corrective feedback approaches for alignment between the tube focal spot, optic, and output focal spot. Sensors are used to detect various operating conditions, and mechanical and/or thermal adjustments are made to correct for instabilities, including misalignments. These types of systems are necessary and valuable for certain applications, but can also increase the cost and complexity of fielded systems.

The above-described XRF technology and systems have been useful in single element analyzers for measuring generally homogeneous sample structure (e.g., sulfur in petroleum products). However, the measurement of toxins in manufactured products presents an additional level of challenges. First, an instrument should have the capability to measure more than one element simultaneously or near-simultaneously, from a relatively confined list of about 10 toxic elements, discussed above. Moreover, manufactured products are likely to be heterogeneous in nature, requiring small spot resolution, as well as the ability to detect toxins in one of a number of heterogeneous layers (e.g., the level of lead in a paint layer and a substrate layer beneath the paint).

Improved x-ray analysis method and systems are required, therefore, to address the problems associated with measuring multiple toxins in potentially heterogeneous samples, to enable in-the-factory and/or in-the-field measurement of toxins in manufactured products.

SUMMARY OF THE INVENTION

The shortcomings of the prior art are overcome and additional advantages are provided by the present invention, which in one aspect is an x-ray analysis apparatus for illuminating a sample spot with an x-ray beam. An x-ray tube is provided having a source spot from which a diverging x-ray beam is produced having a characteristic first energy, and bremsstrahlung energy. A first x-ray optic receives the diverging x-ray beam and directs the beam toward the sample spot, while monochromating the beam; and a second x-ray optic receives the diverging x-ray beam and directs the beam toward the sample spot, while monochromating the beam to a second energy. The first x-ray optic may monochromate characteristic energy from the source spot, and the second x-ray optic may monochromate bremsstrahlung energy from the source spot. The x-ray optics may be curved diffracting optics, for receiving the diverging x-ray beam from the x-ray tube and focusing the beam at the sample spot. Detection is also provided to detect and measure various toxins in, e.g., manufactured products including toys and electronics.

The present inventors have developed these novel and effective techniques to address the growing market need to scrutinize toxins in manufactured goods. Optic-enabled, monochromatic-excited, micro-focus energy-dispersive XRF utilizes the above-discussed advanced x-ray optics together with a low-wattage x-ray tube, commercially available sensors, and proprietary software algorithms in a compact touch-and-shoot design. The optics greatly improve the signal-to-noise and concentrate the intensity in a small spot. The optic-enabled analyzer can nondestructively detect and quantify multiple toxic elements simultaneously in the small features typically found in products such as toys and electronics, regardless of the product's shape, size, or homogeneity. Its simple-to-use design enables the quantifiable measurement of toxin concentrations as low as 1 ppm. The system maintains secure records including clear time-stamped photographic identification of the toy and feature measured, ensuring auditable compliance.

Doubly Curved Crystal (DCC) monochromating optics can be used to enhance measurement intensities by capturing x-rays from a divergent source and redirecting them into an intense focused beam on the surface of the product. Their small spot size allows the analyzer to inspect small features down to 1.5 mm in diameter with no reduction in speed or data quality. This unique capability will distinguish very small features commonly seen in toys and electronics. Regulations require that each material be evaluated separately; the limits are per material and color, not averaging across multiple features.

The favorable signal-to-noise ratio enabled by the optics provides the analyzer with extremely low limits of detection. This high-performance limit-of-detection increases the reliability of results, hence dramatically reducing the number of false positives or negatives. The analyzer will remain effective even at lowest proposed regulatory limits of 40 ppm for lead.

Paint coatings are of particular interest in the toy market so the toy analyzer has incorporated a dedicated coating optic with optimum energy levels and angles to isolate paint layers. Conventional XRF technologies without optics take an average of the coating and substrate layers that can mask high toxin levels in the paint layer. The toy analyzer can distinguish the composition of the paint coating layer from the substrate.

The multi-element capability can simultaneously provide results on the most requested toxins in toys and other consumer products. At least 26 different elements can be detected simultaneously using the system, with emphasis on the 10 toxins of greatest interest to manufacturers including Cr, As, Br, Cd, Sb, Ba, Se, Hg, Cl & Pb.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in combination with the accompanying drawings in which:

BEST MODE FOR CARRYING OUT THE INVENTION

Figure 2:
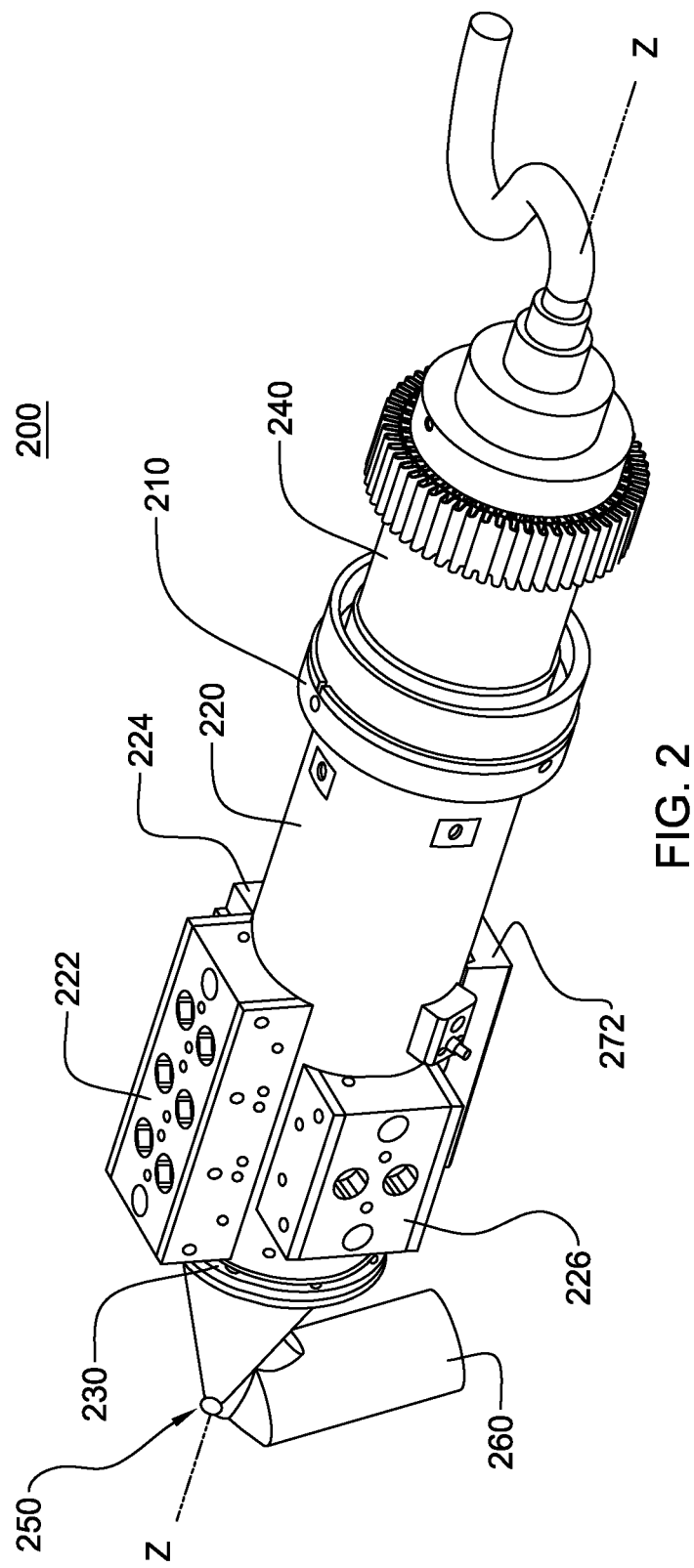
FIG. 2 is a perspective view of an aligned x-ray optic and source assembly, in accordance with one aspect of the present invention.
Figure 3:
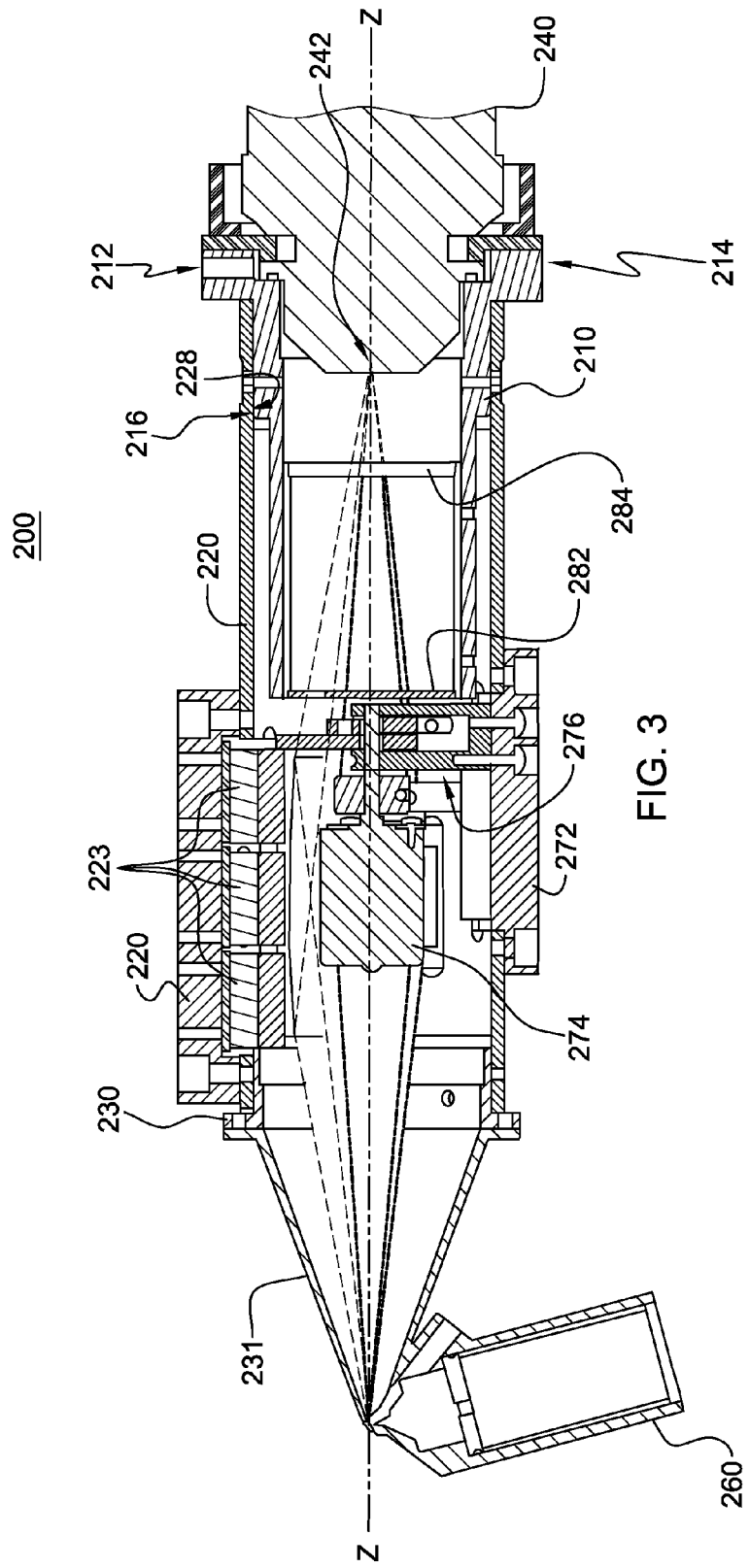
FIG. 3 is a sectional view of the assembly of FIG. 2.
Figure 4:
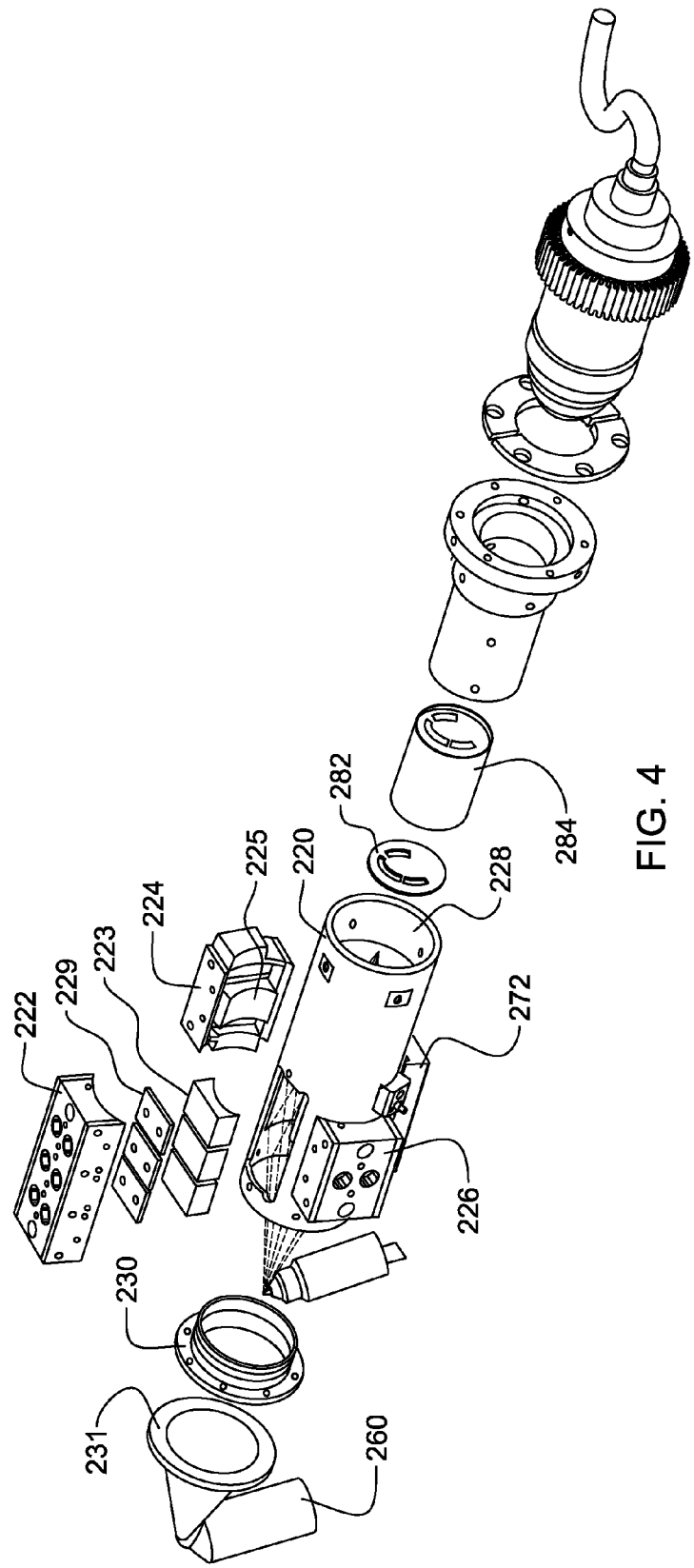
FIG. 4 is an exploded view of the assembly of FIG. 2.

Highly-Aligned X-Ray Source Assembly:

In accordance with the present invention, FIGS. 2-4 depict in various views (using like numerals to refer to like elements) a highly-aligned x-ray optic and source assembly 200 in accordance with the present invention. Various aspects of this package have been disclosed in the commonly assigned, previously-filed U.S. Provisional Applications entitled X-RAY OPTIC AND SOURCE ASSEMBLY FOR PRECISION X-RAY ANALYSIS APPLICATIONS, filed Mar. 5, 2008 as Ser. No. 61/033,899 and HIGHLY ALIGNED X-RAY OPTIC AND SOURCE ASSEMBLY FOR PRECISION X-RAY ANALYSIS APPLICATIONS, filed Mar. 25, 2008 as Ser. No. 61/039,220, each of which is incorporated by reference herein in its entirety.

Figure 1A:
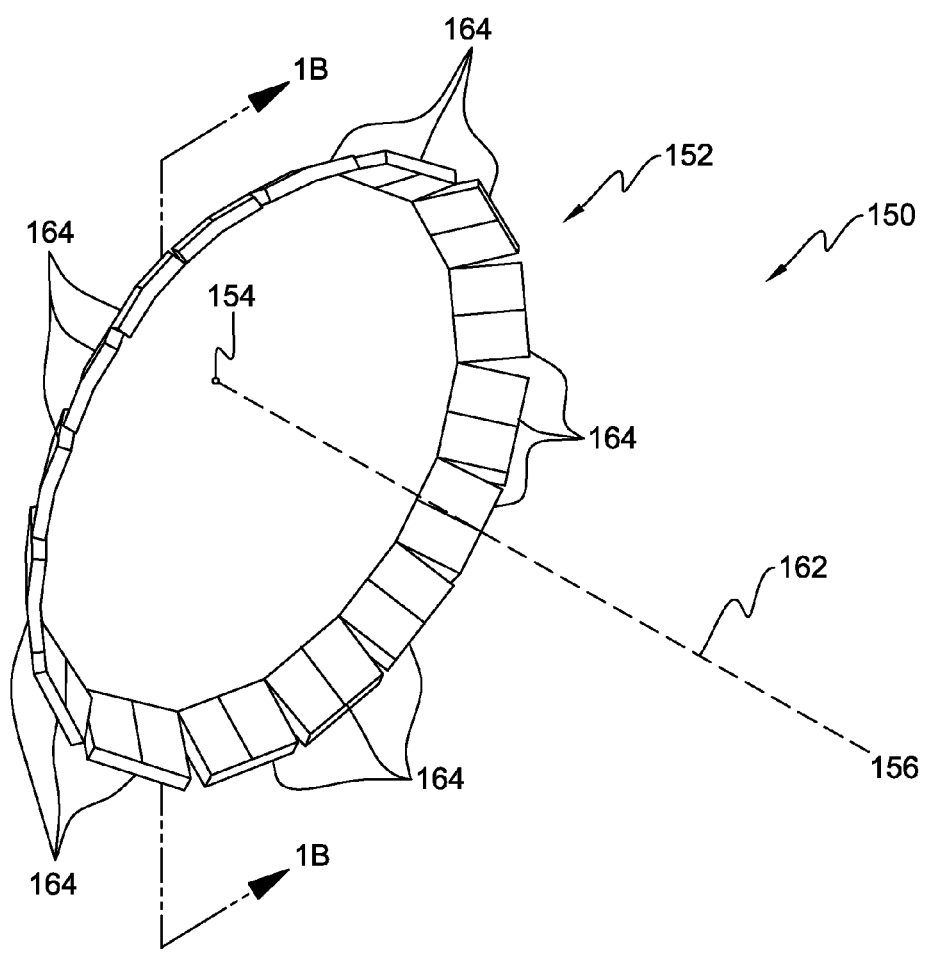
FIGS. 1a-b depict an exemplary arrangement of crystal x-ray optics about an axis, requiring alignment.
Figure 1B:
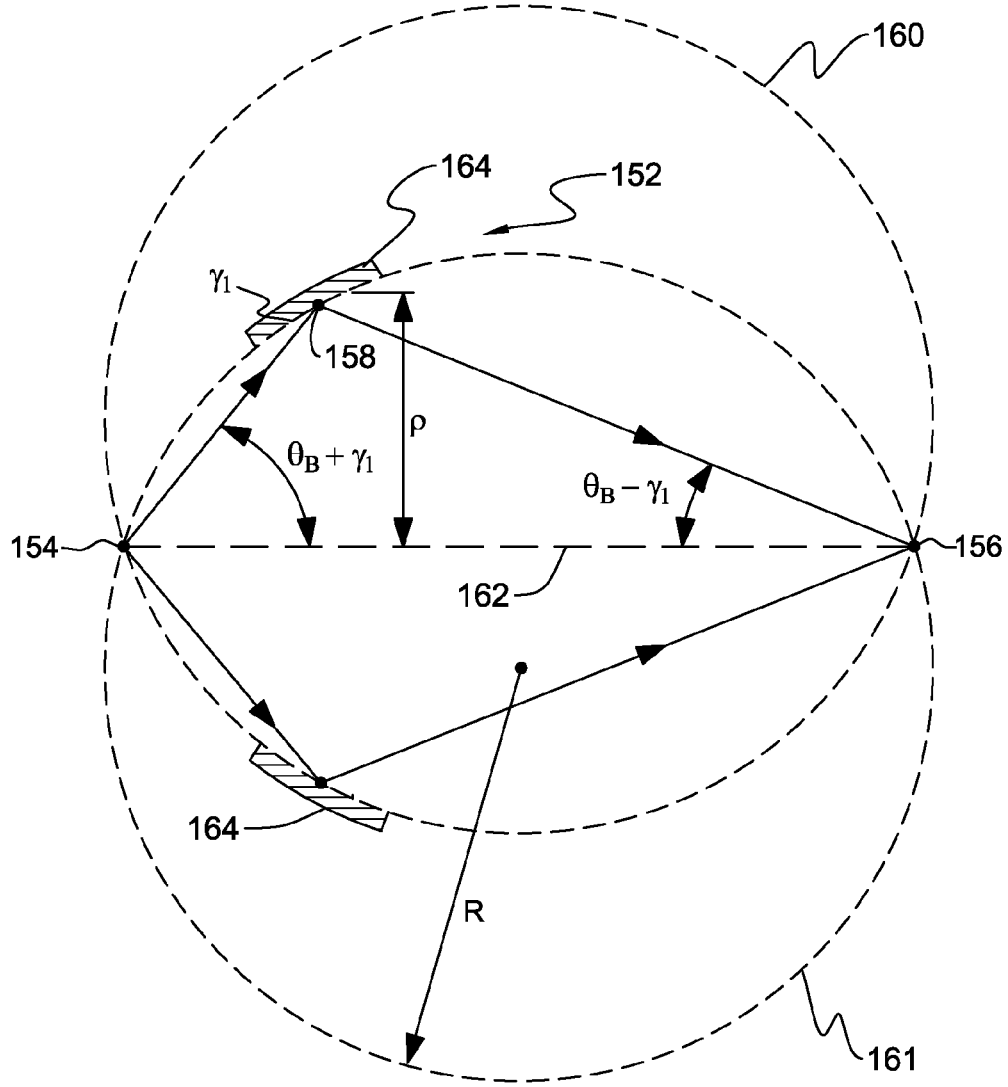

As discussed in those Applications, the assembly includes a first section 210, second section 220, and third section 230, which together align an x-ray tube 240 to a sample spot 250, along a central transmission axis Z. Also aligned along this axis are multiple optic carriage assemblies 222, 224, and 226 which hold exemplary monochromating optics also requiring alignment to transmission axis Z (as discussed above with respect to FIGS. 1a-b).

First housing section 210 may include adjustable tube-mounting features 212, 214 about its perimeter for adjustably mounting tube 240 thereby ensuring centering of tube x-ray spot 242 centrally along a central axis of section 210 (not shown). As discussed below, further attachment of assembly sections 210, 220, and 230 will ensure that each respective section's axis (not shown) is ultimately aligned to the transmission axis Z. Therefore, the present invention allows for incremental alignment of potentially disparate components along the central transmission axis Z. For x-ray tube 240, they may be shipped with slightly off-center tube spots from the manufacturer, and therefore are required to be re-centered along section 210's axis using adjustable mounting features 212 and 214 (e.g., set screws).

The ability to provide an efficient, economical, portable analysis capability depends to a large extent upon x-ray tube and optic technology. In that regard, certain tube and optic technology can be combined for smaller, portable systems, e.g., a compact, electron-bombardment x-ray tube. One example of this type of x-ray tube is available from Oxford Instruments—model # 5011, which operates at less than 100 watts (i.e., 75 watts) at a cost of less than $1500 per tube, in contrast to higher-power, laboratory sources which can cost many thousands, or hundreds of thousands of dollars—which is cost prohibitive for many applications. Another example is the Varian VF-50J (similar to that depicted here), tubular in shape, and which operates at 50 watts or less, at a cost of several thousand dollars each, with a molybdenum material, as discussed further below.

Second housing section 220 includes additional alignment features. First, complimentary mating surfaces 216 and 228 (FIG. 4) are provided to align the axes of sections 210 and 220 upon assembly, i.e., upon insertion of tube section 210 into section 220. Sections 210 and 220 are separately fabricated to guarantee alignment along their axes, and therefore to the central axis Z, when the mating surfaces are in contact.

Sections 210, 220, and 230 are shown in a form of tubular shape. Specifically, the sections are shown in the approximate form of a cylinder, with a circular cross-section, which is one type of tubular shape. The cross-section of tubular sections 210 and 220 could also be square, rectangular, etc. The tubular shapes shown, with circular cross-sections, provide a section-section alignment technique using outer perimeter mating surface 216 of section 210 and inner perimeter mating surface 218 of section 220. The fully enclosed tubular sections also provide required x-ray shielding.

Second, section 220 also accommodates the attachment of optic carriages 222, 224, and 226, which are fabricated to adjustably mount and align x-ray optics 223, 225, and 227 (not shown but implied within carriage 226) respectively, to section 220 and, ultimately, to transmission axis Z. X-ray beam focusing and/or monochromating can be accomplished using certain focusing and/or collimating optics, for example, curved crystal monochromating optics such as those disclosed in commonly assigned U.S. Pat. Nos. 6,285,506; 6,317,483; and 7,035,374; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Each of the above-noted patents is incorporated herein by reference in its entirety. Of particular interest are curved monochromating optics (discussed above with reference to FIGS. 1*a-b*), which require precise alignment along, and a certain distance from, the transmission axis to meet the appropriate Bragg conditions of interest. Also of particular interest is the requirement to align multiple such optics (e.g., 223, 225, 227) along a single Z axis.

The exemplary curved crystal optics 223, 225, and 227 within the second housing section receive the diverging x-ray beam from x-ray tube spot 242, and focus diffracted beam(s) to sample spot 250. The carriages 222, 224, and 226 are mountable either directly or indirectly to the second housing section, such that an active surface of the optic is aligned along, and positioned a desired distance from, the transmission axis Z. The outer surface area (e.g., outer diameter) of the second housing section to which the carriage is mounted can be appropriately sized (e.g., by outer radius) and fabricated such that the at least one x-ray optic is positioned the desired distance from the transmission axis. Moreover, a shim 229, and/or other spacing adjusters (set screws, etc) can be employed to ensure proper optic alignment (FIGS. 3-4). Notably, these types of optics, to maintain their Bragg condition conditions, may be mounted along a surface of the second housing section, while separated from the transmission axis Z.

Third housing section 230 includes an aperture at its point, which requires alignment to transmission axis Z for proper illumination of sample spot 250 with the focused x-ray beam(s) from the optic(s). A cone 231 within this section may also be included for additional shielding, rigidly or adjustably mounted to section 230. Section 230 may also have rigidly mounted thereon an exemplary energy-dispersive detector 260 which itself requires close alignment to transmission axis Z. To effect alignment of section 230 with sections 220 and 210 (thereby completing alignment of the entire source assembly along transmission axis Z), complimentary mating surfaces and/or adjustable mounting means (e.g., set screws) can be employed to align housing section 230 to section 220 and therefore to section 210. Section 230 and/or cone 231 can also be adjusted in directions orthogonal to the transmission axis Z. Other types of detectors (e.g., wavelength dispersive) may also be used with or without similar optics in the detection path. Additional issues should be considered regarding detector alignment. Energy dispersive detector 260 may also have its own focal spot in space, which also requires alignment to beam/sample focal spot 250 (e.g., FIGS. 2-3). (Sample spot 250 may be at the surface, or below the surface, of the sample; depending on the focal point of the x-ray beam.) As shown, detector is mounted to cone 31, which may have adjustable mounting means (shims, set screws, etc.), as well as a predetermined mating surface, which ensure alignment of the detector. Using this approach, end-to-end alignment of the x-ray tube, optic(s), sample spot, and detector is provided.

Additional shims can be placed between each section (210, 220, 230) to control their respective spacings and therefore their longitudinal placement along transmission axis Z.

Also shown is an automated shutter system having its own carriage 272, motor 274 and shutter plates 276. This shutter can be used for x-ray safety purposes (i.e., full blocking shutter), and also for selecting which x-ray beams (from the optics) should be applied to the sample, in any mix ranging from individual non-simultaneous excitation, to full simultaneous excitation, or any mix thereof. This is especially important for the multiple-energy excitation techniques discussed below.

Other blocking slits 282 and 284 can also be provided along the beam path to tailor the beam striking the optics, and reduce other noise and/or scatter.

The above approach provides a highly aligned x-ray optic and source assembly using various techniques to ensure alignment of disparate components (optics, x-ray tubes, detectors, etc) in a small, rugged, portable, analyzer for in-situ, on-line, measurements in industrial process, clinical, and field settings. Volume manufacturing is enabled, even when components of varying dimensional tolerances are introduced into the production. Moreover, the highly aligned assembly provides the precision alignment required by focusing, diffractive optics according to Bragg conditions. Any mis-alignment of the optics will directly impact the precision of the device.

Figure 5A:
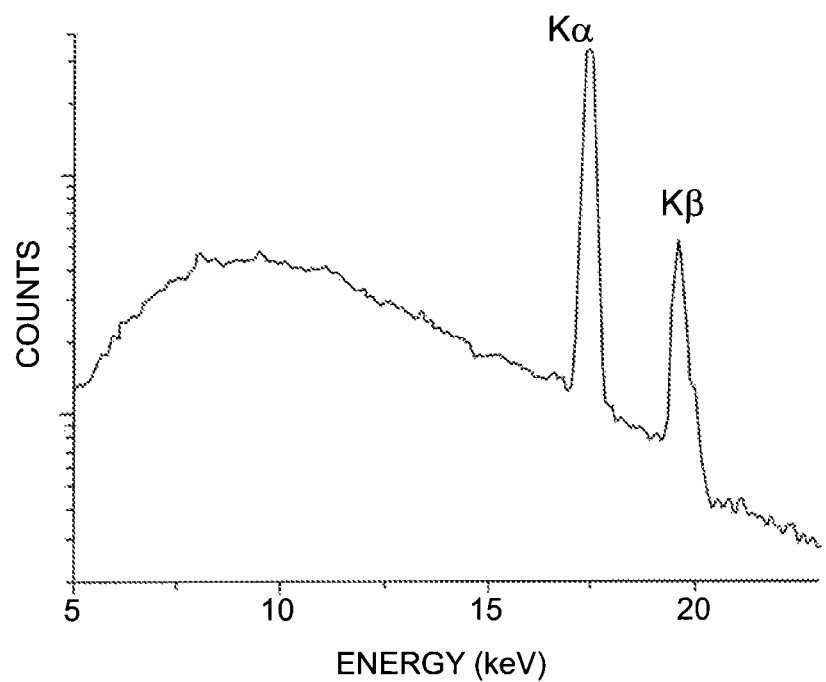
FIGS. 5a-b show the typical characteristic line and bremsstrahlung radiation from an x-ray tube.
Figure 5B:
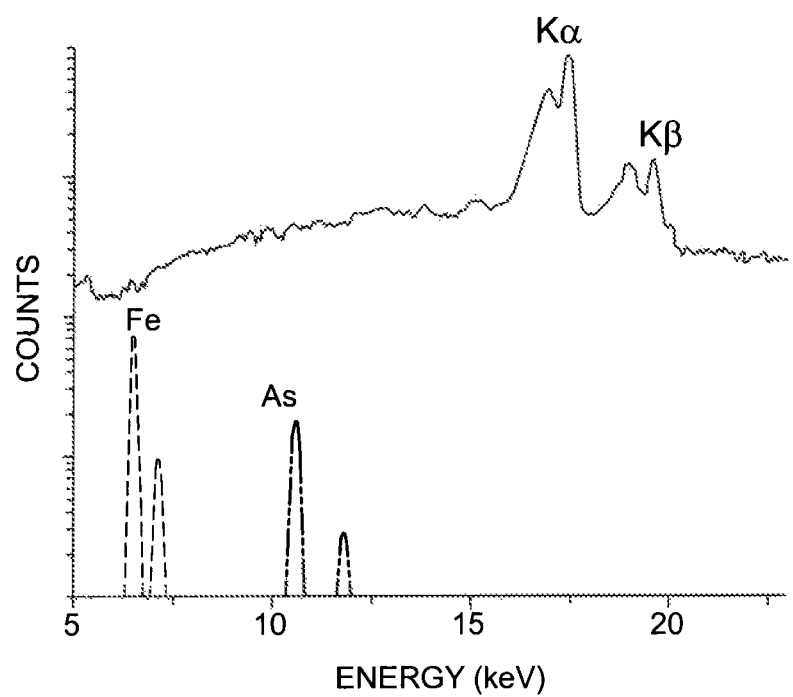
Figure 6A:
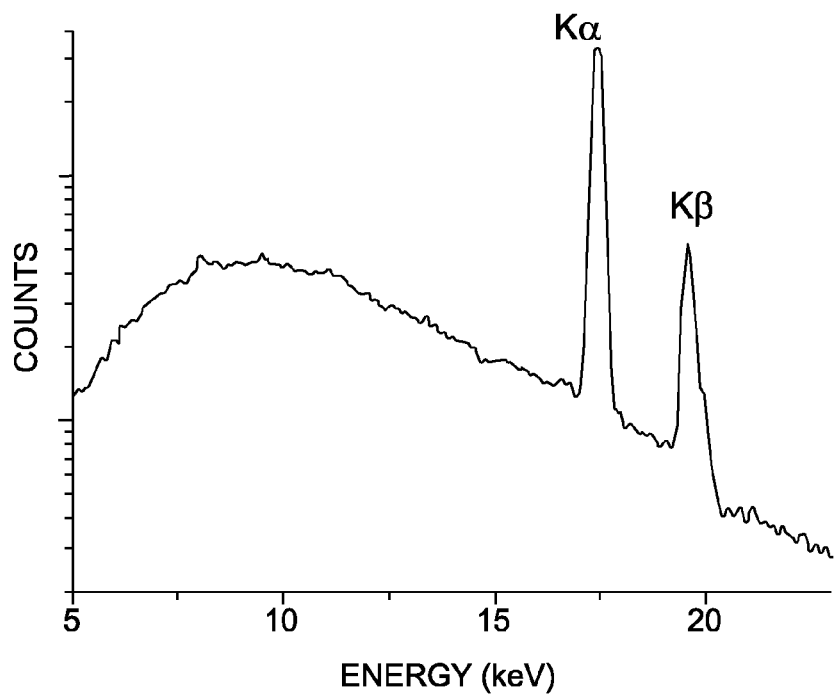
FIGS. 6a-b show the impact of monochromating the x-ray tube energy and the improved detection results.
Figure 6B:
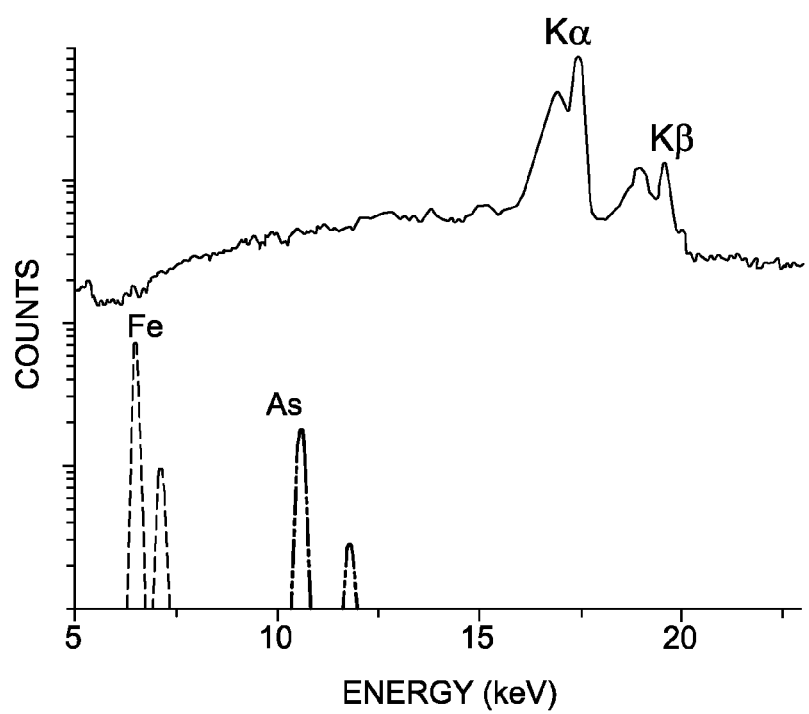

Monochromating Optics at Different Energies:

The benefit of using a monochromatic excitation beam for XRF in such a package can be better understood with reference to the output spectrum of a typical x-ray molybdenum target tube shown in FIG. 5*a*-showing characteristic lines from the tube's target material at about 17 keV, and a broader bremsstrahlung radiation spectrum. When this x-ray beam impinges on a sample, the secondary x-rays emitted from the sample have two components: the fluorescent characteristic lines of the elements in the sample and scattered x-rays from the source as shown in FIG. 5*b*. An energy dispersive (ED) detector measures the sum of the two. Therefore, the fluorescence signals of trace elements in the sample can be obscured by the background. Using a point-focusing, monochromatic optic between the source and the sample, the optic only diffracts the tube's characteristic line from the source. Therefore the spectrum of the beam that impinges on the sample is much simpler, as shown in FIG. 6*a*. The spectrum that emerges from the sample now has a much lower background at all energies except at the Compton scattering region. FIG. 6b illustrates the scattering spectrum with the fluorescence signal from a sample. The trace element signals undetected in FIG. 5b are now clearly detectable.

In accordance with another aspect of the present invention, multiple optics 223 and 225 (and others) of apparatus 200 may be different, i.e., may be tuned to different parts of the x-ray energy spectrum, to optimize element detection and quantification in respective areas of the x-ray energy band. In general, for an element to fluoresce and therefore be subject to detection and measurement, the excitation energy must be at or above the element's x-ray absorption edge. Causing all of the elements of interest to fluoresce therefore requires an excitation energy above the absorption edges of all of the elements of interest.

Figure 7A:
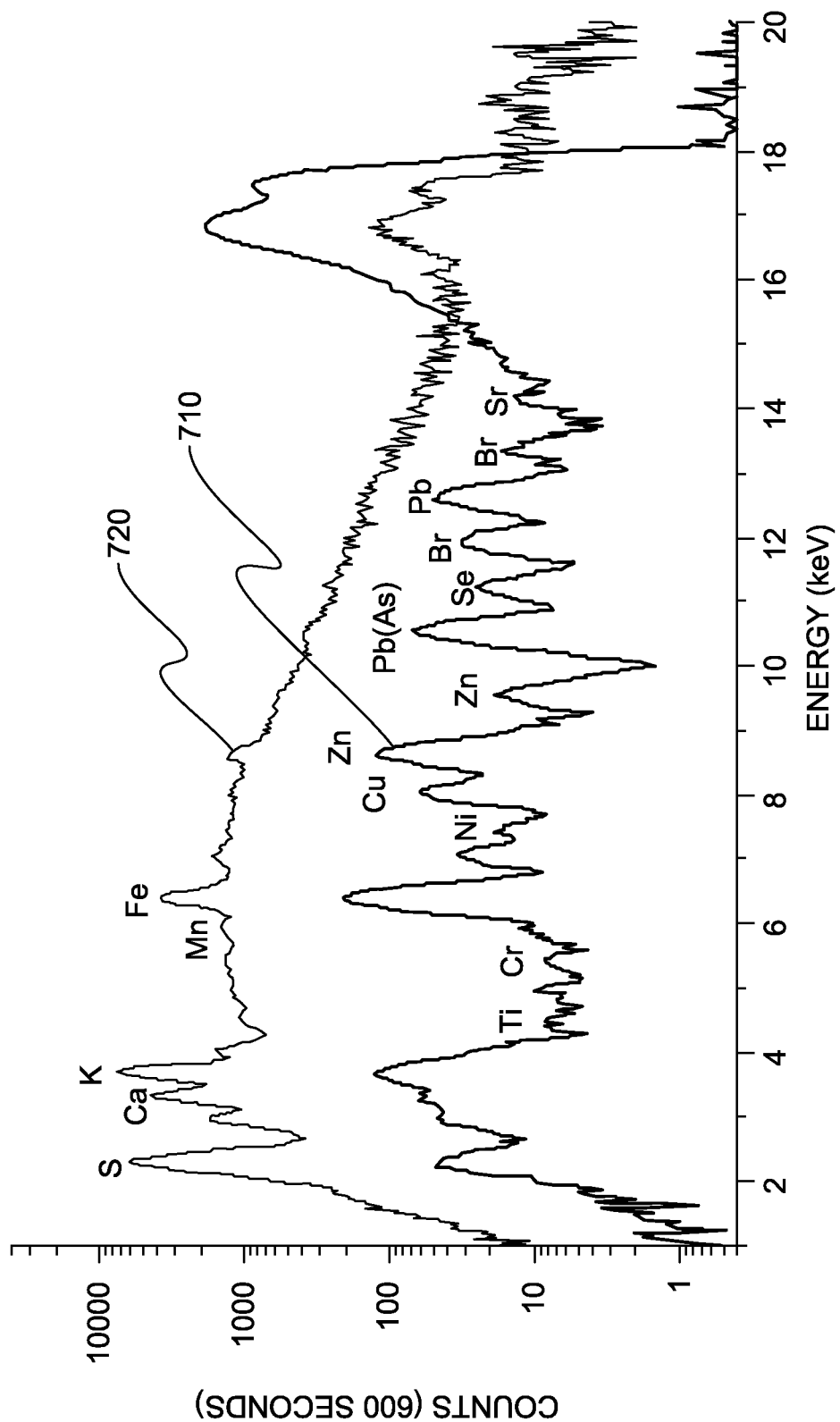
FIGS. 7a-b show the various element peaks due to monochromated excitation energy, and the potential placement of multiple, monochromatic excitation energy beams, in accordance with the present invention.

With reference to the comparative graph of FIG. 7a, this graph shows initially that an optic producing monochromatic excitation improves elemental detection by orders of magnitude (trace 710) versus the conventional polychromatic excitation (trace 720).

Figure 7B:
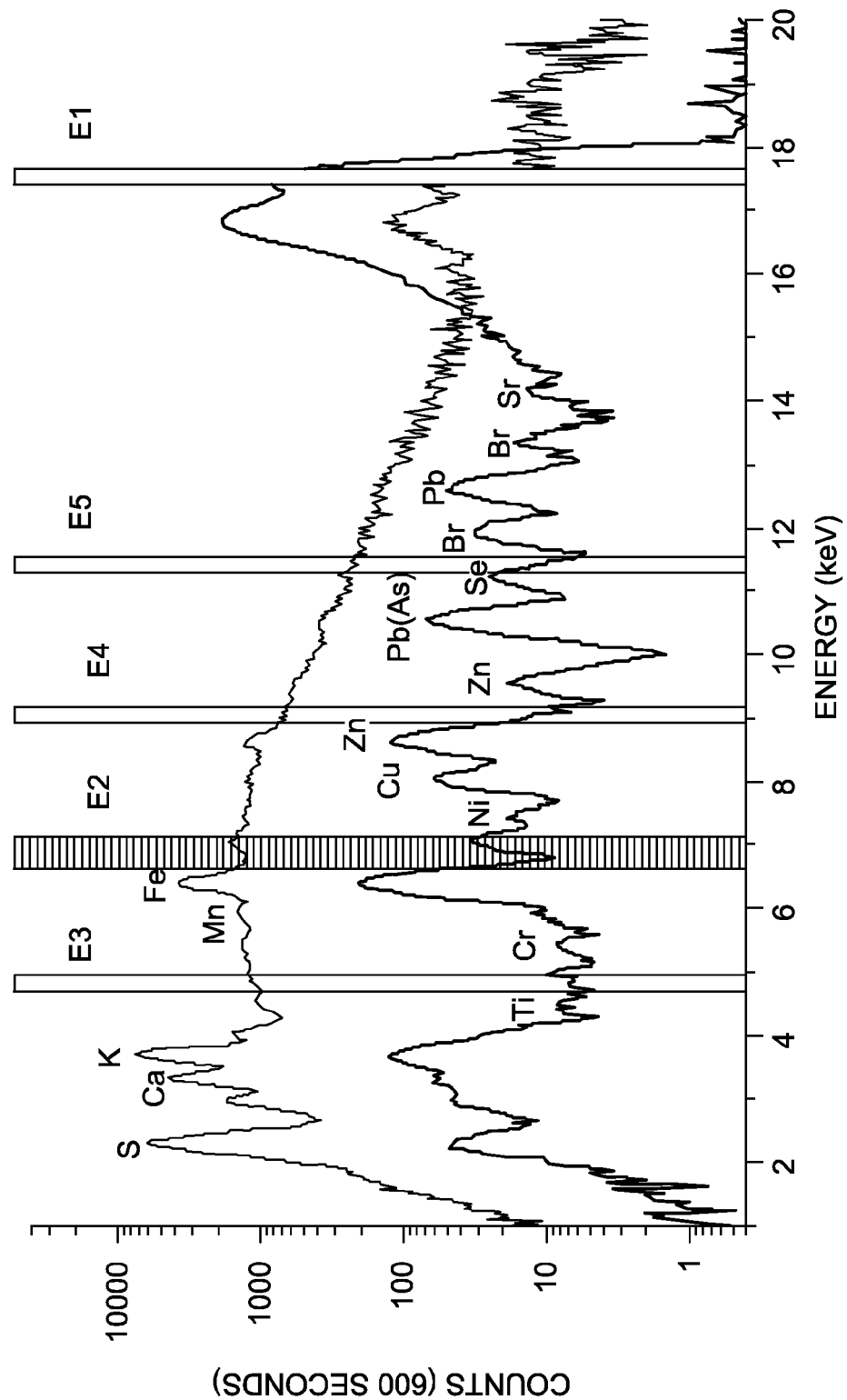

As discussed above, and with further reference to FIG. 7b, a characteristic energy line E1 from, e.g., a molybdenum target x-ray tube at approximately 17 keV, is focused to the sample using a point-focusing, monochromating optic as discussed above, generally causing all elements having fluorescent lines of interest lower that 17 keV to fluoresce (e.g., trace 710). Its excitation effect gradually diminishes, however, for elements having fluorescence lines much lower (e.g., less than 10 keV in this example).

In accordance with the present invention, additional optic(s) can be employed to simultaneously capture the non-characteristic, broad bremsstrallung energy transmitted from the same x-ray tube, and provide additional lines of excitation energy, at e.g., energies E2, E3, E4, E5 . . . each line from a respective point-focusing, monochromating optic. Energies higher than 17 keV (not shown) can also be used. This technique can be used for efficient, low-background excitation of various ranges of elements in the periodic table.

Figure 8:
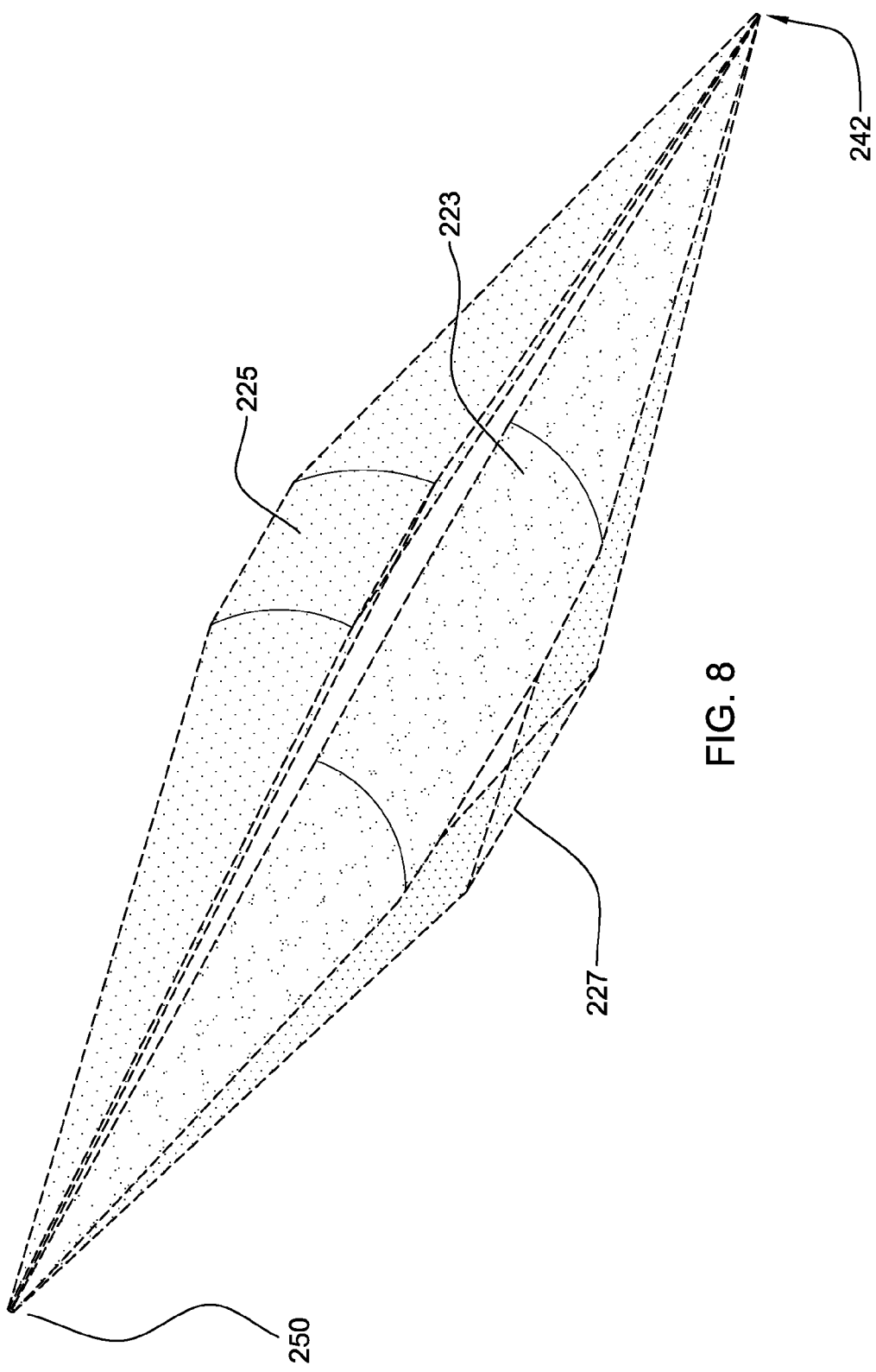
FIG. 8 is a schematic of the x-ray paths established by three different focusing, monochromating x-ray optics in accordance with the present invention.

In the particular system embodiment 200 shown herein and with further reference to the x-ray path diagram of FIG. 8, three optics 223, 225, and 227 provide the 31 keV (from bremsstrallung), the 17 keV characteristic molybdenum line, along with the 7 keV line (also from bremsstrahlung), respectively.

These lines provide optimized excitation of the following approximate ranges of elements of interest from the periodic table (listed along with their atomic numbers):

31 keV: From about Zr (40) to Te (52)

17 keV: From about Cl (17) to Br (35); Rb(37) to Sr(38); Zr(40);

Cs(55) to Bi(83); Th(90); U(92)

7 keV: From about Al (13) to Co (27)

By using different optics, different excitation angles and/or energies can be simultaneously (or sequentially, or any mix thereof using a shutter system) applied to the sample. Because different energies cause different fluorescence effects, more information can be determined in the detection path. For example, higher energies penetrate deeper depths and can be used to detect substrate (rather than painted) layers in the material. Moreover, even though lower energies may penetrate the paint levels, the resultant fluorescence may not, giving more insight into material makeup.

Certain elements exist in the energy band at spacings that generally exceed a detector's ability to resolve (e.g., Cd and Sn), and in fact have overlapping K/L lines and absorption energies. And tin (Sn), a commonly used lead substitute, may mask the cadmium in the detection path. Therefore, excitation just below the absorption of the higher element (Sn), thereby not exciting the tin but effectively exciting all the cadmium, can be used to isolate the lower element (Cd).

Ratios of fluorescence spectra caused by two different excitation energies can also be exploited for additional information about the sample.

Figure 9:
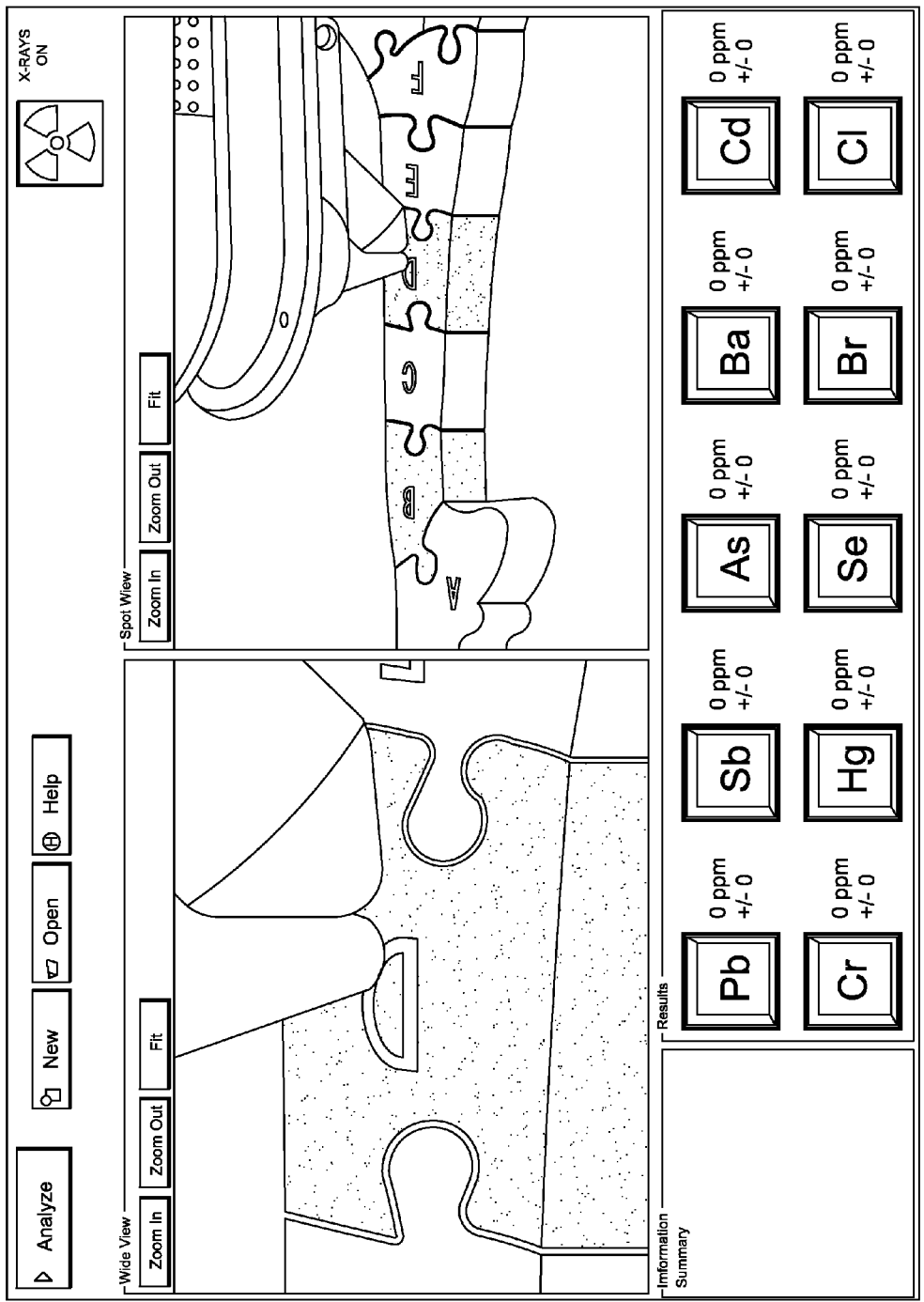
FIG. 9 shows an exemplary excitation of a sample toy with the proposed apparatus in accordance with the present invention, for measuring 10 elements of interest.

FIG. 9 shows an exemplary excitation of a sample toy with the proposed apparatus in accordance with the present invention, for measuring 10 elements of interest.

Multi-element optics (e.g., 223) can be used in accordance with the above-incorporated U.S. Pat. No. 7,035,374. Moreover, layered optics can be used, in accordance with multi-layer techniques, and/or multi-crystal-layer techniques as disclosed in U.S. patent application Ser. No. 11/941,377 filed on Nov. 16, 2007 entitled X-RAY FOCUSING OPTIC HAVING MULTIPLE LAYERS WITH RESPECTIVE CRYSTAL ORIENTATIONS, the entirety of which is incorporated by reference. Such DCCs are referred to herein as LDCCs. There are several unique features of LDCC optics. The rocking curve width of the optic can be designed to be 2 to 5 times higher than single layer DCC optics. This will increase the bandwidth and provide flux increase for slicing the bremsstrahlung spectrum. For a single layer Si or Ge DCC, the rocking curve can be narrow such that its efficiency is reduced by the finite size of a typical x-ray point source. The LDCC can be designed to match the source size and improve the transmitted flux for focusing characteristic lines as well. The LDCC optics may also work better for higher energy photons. A more layered structure can be built for high energy x-rays due to reduced absorption. The useful energy range for the LDCC is expected to be 6-50 keV.

In one particular example, three LDCC optics can be used to provide a tri-chromatic focused beam from a small spot Cu target source. The first LDCC focuses Cu K$\alpha$1 8.04 keV characteristic x-rays to the sample spot. The spot size is approximately 50 μm to 75 μm. The Cu LDCC covers the excitation for elements from Silicon (Si) to Manganese (Mn) including Cr. The second LDCC selects and focuses a band of bremsstrahlung centered at 16 keV for Hg, Pb and Br excitation. The third LDCC selects and focuses a band of bremsstrahlung centered at 28 keV for Cd excitation. The two bremsstrahlung optics have focused spots of 100 μm to 300 μm. The bandwidth of the bremsstrahlung optics are designed to be about 1-2% of the focusing energy. A PIN diode detector is used for EDXRF spectrometry. A shutter scheme can be constructed between the x-ray source and the optics, or between the optics and the sample (as discussed above) to have the option to turn the beam from each optic on and off, in any combination. A camera and/or laser spot can be placed in the center of the three optics in order to visually locate the measurement spot. The camera will also be used to store the image along with the spectral data. A small laser-height gauge is used to aid in the positioning of the sample at the focal point.

The trend toward increasing global regulation of toxins presents an opportunity for such highly aligned systems as a platform technology to address a number of currently important applications. The disclosed system provides several advantages over previous toxin detection technologies with the combined ability to non-destructively detect very low levels, isolate small features, and give reliable results across a wide range of toxic elements. Conventional XRF analyzers and more standard analytical chemistry techniques do not possess the needed combination of reliable results, some level of portability, and low cost per test needed in today's tightening regulatory environment. Areas that are in need of these attributes include consumer products, electronics, air quality monitoring, body fluids, food products, and pharmaceuticals. Many of these applications can, in principle, share a common hardware and software platform, to hasten new product introductions, lower manufacturing costs, and provide higher quantities of precision instruments.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray analysis apparatus for illuminating a sample spot with an x-ray beam, comprising;
    an x-ray tube having a source spot from which a diverging x-ray beam is produced having a characteristic first energy, and bremsstrahlung energy;
    a first x-ray optic for receiving the diverging x-ray beam and directing the beam toward the sample spot, the first x-ray optic monochromating the beam;
    a second x-ray optic for receiving the diverging x-ray beam and directing the beam toward the sample spot, the second x-ray optic monochromating the beam to a second energy; and
    wherein the source spot requires alignment along a transmission axis passing through the sample spot, the apparatus further comprising:
        a first tubular housing section to which the x-ray tube is attached along a first axis thereof such that the source spot coincides with the first axis, the first housing section further including mating surfaces aligned to the first axis;
        a second tubular housing section having a second axis coinciding with the transmission axis, and mating surfaces aligned to the second axis; and
        the first and second x-ray optics attached to the second housing section for receiving the diverging x-ray beam and directing the beam toward the sample spot, the first and second optics requiring alignment along the transmission axis;
        the first housing section and the second housing section being matable along their respective mating surfaces to thereby align the first and second axes with the transmission axis, thereby aligning source spot, x-ray optics, and sample spot.

2. The apparatus of claim 1, wherein the first x-ray optic monochromates characteristic energy from the source spot and the second x-ray optic monochromates bremsstrahlung energy from the source spot.

3. The apparatus of claim 1, wherein the x-ray optics are curved diffracting optics, for receiving the diverging x-ray beam from the x-ray tube and focusing the beam at the sample spot.

4. The apparatus of claim 3, wherein the x-ray optics are focusing monochromating optics.

5. The apparatus of claim 4, wherein the focusing onochromatic optics are doubly curved crystal optics or doubly curved multi-layer optics.

6. The apparatus of claim 1, further comprising a third x-ray optic for receiving the diverging x-ray beam and directing the beam toward the sample spot, the third x-ray optic monochromating bremsstrahlung energy from the source spot to a third energy.

7. The apparatus of claim 1, wherein each optic is attached to the second housing section for receiving the diverging x-ray beam and directing a respective portion of the beam toward the sample spot, and requiring alignment along the transmission axis, mounted along a surface of the second housing section, and separated from the transmission axis.

8. The apparatus of claim 1, further comprising a third housing section, the third housing section including an aperture along the transmission axis through which the x-ray beam passes when illuminating the sample spot, the second housing section and third housing section being matable along respective mating surfaces to thereby align the aperture with the transmission axis and therefore the sample spot, the apparatus further comprising an x-ray detector mounted to the third housing section in alignment with the sample spot.

9. The apparatus of claim 1, wherein the first and second housing sections are tubular in shape, and the mating surfaces of the first and second housing sections comprise surface portions in contact with each other upon attachment of the first and second tubular housing sections.

10. The apparatus of claim 9, wherein the x-ray optics are focusing monochromating optics.

11. The apparatus of claim 10, wherein focusing monochromatic optics are doubly curved crystal optics or doubly curved multi-layer optics, mounted along a surface of the second housing section, and separated from the second axis.

12. An x-ray analysis apparatus for illuminating a sample spot with an x-ray beam, comprising:
    an x-ray tube having a source spot from which a diverging x-ray beam is produced, the source spot requiring alignment along a transmission axis passing through the sample spot;
    a first housing section to which the x-ray tube is attached along a first axis thereof, the first housing section including adjustable mounting features for adjustably mounting the x-ray tube therein such that the source spot coincides with the first axis, the first housing section further including mating surfaces aligned to the first axis;
    a second housing section having a second axis coinciding with the transmission axis, and mating surfaces aligned to the second axis; and
    first and second, different x-ray optics attached to the second housing section for receiving the diverging x-ray beam and directing the beam toward the sample spot at different respective energies, the first and second x-ray optics requiring alignment along the transmission axis;
    the first housing section and second housing section being ma able along their respective mating surfaces to thereby align the first and second axes with the transmission axis, thereby aligning the source spot, x-ray optics, and sample spot.

13. The apparatus of claim 12, wherein the first optic monochromates characteristic energy from the source spot and the second x-ray optic monochromates bremsstrahlung energy from the source spot.

14. The apparatus of claim 12, wherein the x-ray optics are curved diffracting optics, for receiving the diverging x-ray beam from the x-ray tube and focusing the beam at the sample spot.

15. The apparatus of claim 14, wherein the x-ray optics are focusing monochromating optics.

16. The apparatus of claim 15, wherein the focusing monochromatic optics are doubly curved crystal optics or doubly curved multi-layer optics.

17. The apparatus of claim 12, further comprising a third x-ray optic for receiving the diverging x-ray beam and directing the beam toward the sample spot, the third x-ray optic monochromating bremsstrahlung energy from the source spot to a third energy.

18. The apparatus of claim 12, wherein the second housing section is tubular in shape, with the second axis running longitudinally therein.

19. The apparatus of claim 12, wherein the x-ray tube is tubular in shape, having its source spot at one end thereof.

20. The apparatus of claim 12, wherein the first and second housing sections are tubular in shape, and the mating surfaces of the first and second housing sections comprise surface portions in contact with each other upon attachment of the first and second tubular housing sections.

21. The apparatus of claim 12, further comprising a carriage for mounting each x-ray optic to the second housing section to receive the diverging x-ray beam, the carriages mountable either directly or indirectly to the second housing section, such that an active surface of x-ray optics are aligned along, and positioned a desired distance from, the transmission axis.

22. The apparatus of claim 21, wherein a surface of the second housing section to which the carriages are mounted are fabricated such that the at least one x-ray optic is positioned the desired distance from the transmission axis.

* * * * *